US012728252B2

(12) United States Patent
Ku et al.

(10) Patent No.: US 12,728,252 B2
(45) Date of Patent: Sep. 8, 2026

(54) CONNECTOR FOR FLEXIBLE TUBING USED FOR FLUID TRANSPORT

(71) Applicant: MD Innovate, LLC, Decatur, GA (US)

(72) Inventors: David Ku, Decatur, GA (US); Susan Shea, McKees Rocks, PA (US); Kevin Maher, Decatur, GA (US); Shriprasad Deshpande, Bethesda, MD (US)

(73) Assignee: MD Innovate, LLC, Decatur, GA (US)

( * ) Notice: Subject to any disclaimer, the term of this patent is extended or adjusted under 35 U.S.C. 154(b) by 0 days.

(21) Appl. No.: 18/538,561

(22) Filed: Dec. 13, 2023

(65) Prior Publication Data

US 2024/0198073 A1 Jun. 20, 2024

Related U.S. Application Data

(60) Provisional application No. 63/432,551, filed on Dec. 14, 2022.

(51) Int. Cl.

| | |
|---|---|
| ***A61M 39/10*** | (2006.01) |
| ***F16L 31/00*** | (2006.01) |
| ***F16L 41/02*** | (2006.01) |

(52) U.S. Cl.

CPC ............. *A61M 39/10* (2013.01); *F16L 31/00* (2013.01); *F16L 41/021* (2013.01)

(58) Field of Classification Search

CPC ................... F16L 31/00; F16L 41/021; A61M 2039/1077; A61M 2039/1033; A61M 39/10; A61M 39/12; A61M 39/105

See application file for complete search history.

(56) References Cited

U.S. PATENT DOCUMENTS

| | | | | |
|---|---|---|---|---|
| 3,876,234 A | | 4/1975 | Harms | |
| 3,945,380 A | * | 3/1976 | Dabney ................. | A61M 39/02 604/410 |
| 4,076,285 A | | 2/1978 | Martinez | |
| 4,398,757 A | | 8/1983 | Floyd et al. | |

(Continued)

FOREIGN PATENT DOCUMENTS

| | | | | |
|---|---|---|---|---|
| JP | 2020065606 A | * | 4/2020 | ............ A61M 39/10 |

OTHER PUBLICATIONS

JP-2020065606-A (Year: 2020).*

(Continued)

*Primary Examiner* — David Bochna

(74) *Attorney, Agent, or Firm* — Meunier Carlin & Curfman LLC

(57) ABSTRACT

Various implementations include a connector for connecting flexible tubing segments. The connector includes a connector body having a first end and a second end disposed opposite one another along a longitudinal axis of the connector body. The connector body defines a first bore, a second bore, and a lumen. The first bore is configured for receiving an end portion of a first flexible tubing segment therein. The first bore has a circular cross-sectional shape and a first diameter. The second bore is configured for receiving an end portion of a second flexible tubing segment therein. The second bore has a circular cross-sectional shape and a second diameter. The lumen extends from the first bore to the second bore. The lumen has a circular cross-sectional shape and a third diameter that is less than each of the first diameter and the second diameter.

18 Claims, 8 Drawing Sheets

(56) References Cited

U.S. PATENT DOCUMENTS

| | | | | |
|---|---|---|---|---|
| 4,790,567 | A | 12/1988 | Kawano et al. | |
| 5,431,456 | A * | 7/1995 | Okumura | F16L 47/04 285/133.4 |
| 5,730,123 | A | 3/1998 | Lorenzen et al. | |
| 6,003,553 | A * | 12/1999 | Wahlberg | A61M 39/10 285/332 |
| 6,290,682 | B1 | 9/2001 | Myers | |
| 6,488,318 | B1 * | 12/2002 | Shim | F16L 19/075 285/353 |
| 7,690,699 | B2 * | 4/2010 | Smahl | F16L 47/24 285/291.1 |
| 8,414,542 | B2 * | 4/2013 | Stroup | A61M 39/12 604/249 |
| 9,482,375 | B2 * | 11/2016 | Paul | F16L 33/224 |
| 10,240,704 | B2 * | 3/2019 | Cassiday | A61M 39/10 |
| 2004/0068239 | A1 | 4/2004 | Utterberg et al. | |
| 2006/0284423 | A1 * | 12/2006 | Katsuno | A61M 39/10 285/417 |
| 2007/0093762 | A1 * | 4/2007 | Utterberg | A61M 39/20 604/256 |
| 2007/0157986 | A1 * | 7/2007 | Lammers | A61M 5/16877 138/40 |
| 2008/0063467 | A1 * | 3/2008 | Ferrari | A61M 39/10 403/169 |
| 2010/0324466 | A1 * | 12/2010 | Chau | A61M 39/045 604/164.08 |
| 2015/0297817 | A1 * | 10/2015 | Guala | A61M 39/10 604/256 |
| 2016/0195208 | A1 * | 7/2016 | Cassiday | F16L 31/02 285/125.1 |
| 2017/0336008 | A1 * | 11/2017 | Hankins | A61M 39/10 |
| 2021/0010622 | A1 * | 1/2021 | Miheli | F16L 41/008 |
| 2022/0184369 | A1 * | 6/2022 | Fontana | A61M 39/10 |

OTHER PUBLICATIONS

Hastings, S., Towards Improved Device Design and Clinical Management: the Thrombogenic Effect of the Fluid Dynamics and Material Surface Relationship, A Dissertation Presented to The Academic Faculty, Georgia Institute of Technology Mar. 2017.

Hastings S, Ku DN, Wagoner S, Maher KO, and Deshpande S. Sources of Circuit Thrombosis in Pediatric Extracorporeal Membrane Oxygenation. ASAIO Journal 2017;63:86-92.

Hastings S, Deshpande S, Wagoner S, Maher K, and Ku DN. Thrombosis in centrifugal pumps: location and composition in clinical and in vitro circuits. International Journal of Artificial Organs 2016;39(4):200-204.

* cited by examiner

CONNECTOR FOR FLEXIBLE TUBING USED FOR FLUID TRANSPORT

CROSS-REFERENCE TO RELATED APPLICATIONS

This application claims priority to U.S. Provisional Patent Application No. 63/432,551, filed Dec. 14, 2022, which is incorporated herein by reference in its entirety

BACKGROUND

Flexible tubing is commonly used for fluid transport in a wide variety of applications. Connectors for flexible tubing facilitate construction of tubing lengths and loops and can provide access to the fluid. Currently, flexible tubing connectors require expansion of the tubing around the connector, causing diameter changes.

Extracorporeal membrane oxygenation (ECMO) is a form of life support and consists of a flexible tubing circuit connected by connectors. Clotting or thrombosis in the circuit is a burdensome clinical problem and connectors may be a contributing source.

Thus, there is a need for a flexible tubing connector that reduces clotting.

SUMMARY

Various implementations include a connector for connecting flexible tubing segments. The connector includes a connector body having a first end and a second end disposed opposite one another along a longitudinal axis of the connector body. The connector body defines a first bore, a second bore, and a lumen. The first bore extends from the first end toward the second end. The first bore is configured for receiving an end portion of a first flexible tubing segment therein. The first bore has a circular cross-sectional shape and a first diameter. The second bore extends from the second end toward the first end. The second bore is configured for receiving an end portion of a second flexible tubing segment therein. The second bore has a circular cross-sectional shape and a second diameter. The lumen extends from the first bore to the second bore. The lumen has a circular cross-sectional shape and a third diameter that is less than each of the first diameter and the second diameter.

In some implementations, the connector body has a non-circular cross-sectional shape defined by one or more external surfaces of the connector body. In some implementations, the connector body has a polygonal cross-sectional shape defined by a plurality of external surfaces of the connector body. In some implementations, the polygonal cross-sectional shape is a hexagonal cross-sectional shape.

In some implementations, the connector body comprises a plurality of planar external surfaces. In some implementations, the connector body comprises a plurality of ribs each extending along one or more external surfaces of the connector body. In some implementations, the plurality of ribs includes a first rib spaced apart from each of the first end and the second end and a second rib spaced apart from the first rib and from each of the first end and the second end. In some implementations, each of the ribs extends perpendicular to the longitudinal axis. In some implementations, each of the ribs forms a ring extending around the longitudinal axis.

In some implementations, the first diameter is equal to the second diameter. In some implementations, the first diameter is different than the second diameter.

In some implementations, the first bore has a first length in the direction of the longitudinal axis. The second bore has a second length in the direction of the longitudinal axis. In some implementations, the first length is equal to the second length. In some implementations, the first length is different than the second length.

In some implementations, the lumen has a third length in the direction of the longitudinal axis. In some implementations, the third length is less than each of the first length and the second length. In some implementations, the third length is greater than each of the first length and the second length.

In some implementations, the first diameter is constant along an entire length of the first bore in the direction of the longitudinal axis, and the second diameter is constant along an entire length of the second bore in the direction of the longitudinal axis. In some implementations, the third diameter is constant along an entire length of the lumen in the direction of the longitudinal axis.

In some implementations, the lumen varies in diameter along at least a portion of a length of the lumen in the direction of the longitudinal axis.

In some implementations, the lumen includes a first portion extending from the first bore and having a constant diameter and a second portion extending from the first portion to the second bore and having a varying diameter in the direction of the longitudinal axis. In some implementations, the diameter of the second portion varies in a linear manner in the direction of the longitudinal axis. In some implementations, the diameter of the second portion varies in a non-linear manner in the direction of the longitudinal axis.

In some implementations, the lumen varies in diameter along an entire length of the lumen in the direction of the longitudinal axis. In some implementations, the diameter of the lumen varies in a linear manner in the direction of the longitudinal axis. In some implementations, the diameter of the lumen varies in a non-linear manner in the direction of the longitudinal axis.

In some implementations, the connector further includes a luer body configured for removably coupling with a mating luer adapter. In some implementations, the luer body is coupled to the connector body and extends perpendicular to the longitudinal axis. In some implementations, the luer body defines a second lumen in fluid communication with the lumen of the connector body. In some implementations, the luer body is centered between the first end and the second end. In some implementations, the connector body and the luer body are integrally formed with one another. In some implementations, the connector is formed of a polymer.

Various implementations include an assembly. The assembly includes a connector, a first flexible tubing segment, and a second flexible tubing segment. The connector includes a connector body having a first end and a second end disposed opposite one another along a longitudinal axis of the connector body. The connector body defines a first bore, a second bore, and a lumen. The first bore extends from the first end toward the second end. The first bore has a circular cross-sectional shape and a first diameter. The second bore extends from the second end toward the first end. The second bore has a circular cross-sectional shape and a second diameter. The lumen extends from the first bore to the second bore. The lumen has a circular cross-sectional shape and a third diameter that is less than each of the first and second diameter. The first flexible tubing segment includes a first end portion received within the first bore. The first flexible tubing segment has a first outer diameter and a first inner diameter. The first inner diameter is equal to a diameter of the lumen adjacent the first bore. The second flexible tubing segment includes a second end portion received within the second bore. The second flexible tubing segment has a second outer diameter and a second inner diameter. The second inner diameter is equal to a diameter of the lumen adjacent the second bore.

In some implementations, the connector body has a non-circular cross-sectional shape defined by one or more external surfaces of the connector body. In some implementations, the connector body has a polygonal cross-sectional shape defined by a plurality of external surfaces of the connector body. In some implementations, the polygonal cross-sectional shape is a hexagonal cross-sectional shape.

In some implementations, the connector body comprises a plurality of planar external surfaces. In some implementations, the connector body comprises a plurality of ribs each extending along one or more external surfaces of the connector body. In some implementations, the plurality of ribs includes a first rib spaced apart from each of the first end and the second end and a second rib spaced apart from the first rib and from each of the first end and the second end. In some implementations, each of the ribs extends perpendicular to the longitudinal axis. In some implementations, each of the ribs forms a ring extending around the longitudinal axis.

In some implementations, the first diameter is equal to the second diameter. In some implementations, the first diameter is different than the second diameter.

In some implementations, the first bore has a first length in the direction of the longitudinal axis. The second bore has a second length in the direction of the longitudinal axis. In some implementations, the first length is equal to the second length. In some implementations, the first length is different than the second length.

In some implementations, the lumen has a third length in the direction of the longitudinal axis. In some implementations, the third length is less than each of the first length and the second length. In some implementations, the third length is greater than each of the first length and the second length.

In some implementations, the first diameter is constant along an entire length of the first bore in the direction of the longitudinal axis, and the second diameter is constant along an entire length of the second bore in the direction of the longitudinal axis. In some implementations, the third diameter is constant along an entire length of the lumen in the direction of the longitudinal axis.

In some implementations, the lumen varies in diameter along at least a portion of a length of the lumen in the direction of the longitudinal axis.

In some implementations, the lumen includes a first portion extending from the first bore and having a constant diameter and a second portion extending from the first portion to the second bore and having a varying diameter in the direction of the longitudinal axis. In some implementations, the diameter of the second portion varies in a linear manner in the direction of the longitudinal axis. In some implementations, the diameter of the second portion varies in a non-linear manner in the direction of the longitudinal axis.

In some implementations, the lumen varies in diameter along an entire length of the lumen in the direction of the longitudinal axis. In some implementations, the diameter of the lumen varies in a linear manner in the direction of the longitudinal axis. In some implementations, the diameter of the lumen varies in a non-linear manner in the direction of the longitudinal axis.

In some implementations, the connector further includes a luer body configured for removably coupling with a mating luer adapter. In some implementations, the luer body is coupled to the connector body and extends perpendicular to the longitudinal axis. In some implementations, the luer body defines a second lumen in fluid communication with the lumen of the connector body. In some implementations, the luer body is centered between the first end and the second end. In some implementations, the connector body and the luer body are integrally formed with one another. In some implementations, the connector is formed of a polymer.

DETAILED DESCRIPTION

Figure 1A:
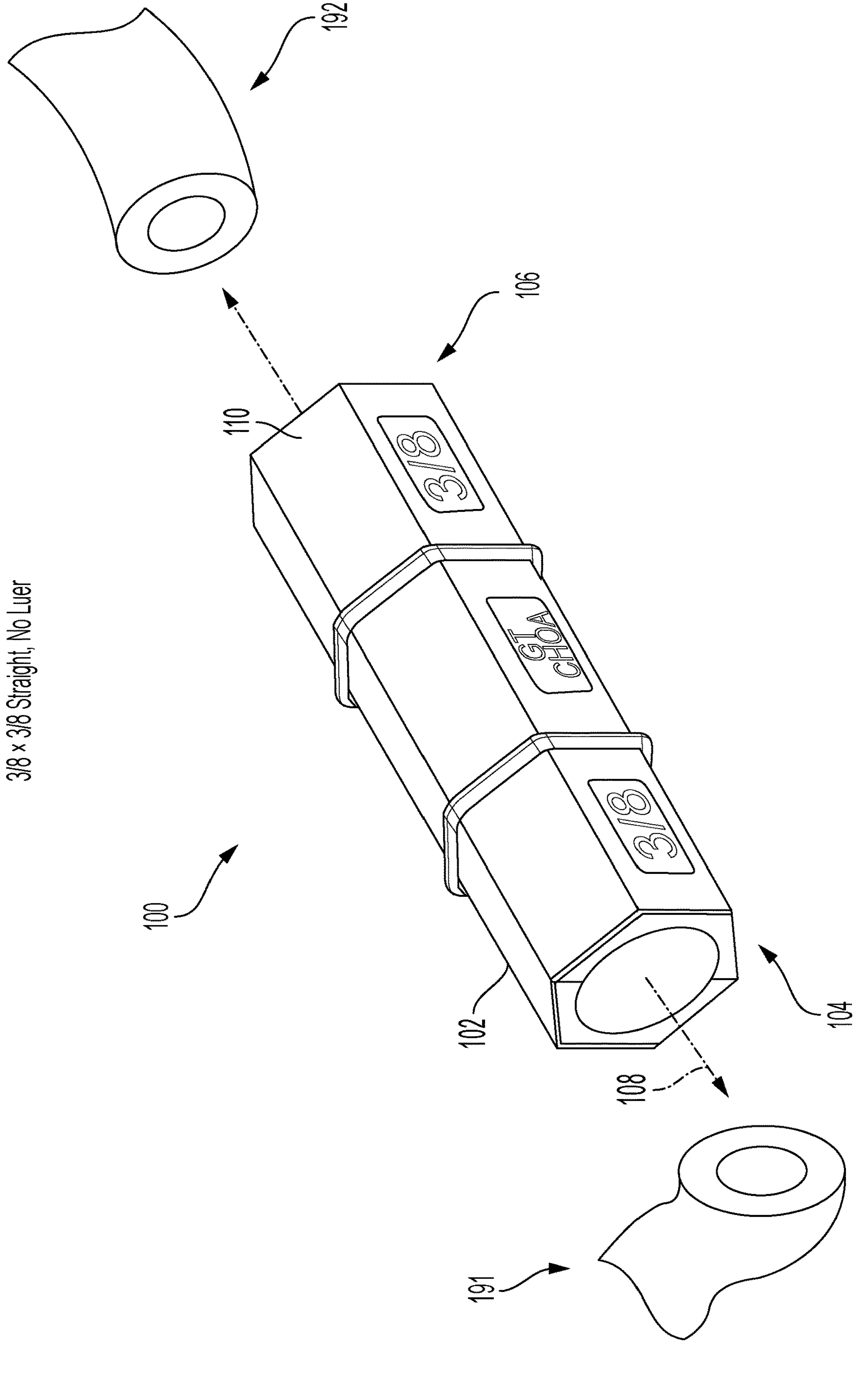
FIG. 1*a* shows a perspective view of a connector.

The devices, systems, and methods disclosed herein provide for a flexible tubing connector which reduces incidence of clotting and thrombosis in flexible tubing circuits. Extracorporeal membrane oxygenation (ECMO) is a form of life support and consists of a flexible tubing circuit connected by connectors. Connectors for flexible tubing facilitate construction of tubing lengths and loops and can provide access to the fluid. Clotting or thrombosis in the circuit is a burdensome clinical problem and connectors may be a contributing source. Current flexible tubing connectors require expansion of the tubing around the connector, causing diameter changes.

Sudden expansions and contractions in the tubing created by the connectors potentiate thrombus formation. Changes in the tubing diameter can create zones of low shear rates in the fluid and/or zones of recirculation or stagnation. Thrombus growth directly co-locates with these areas of low shear, recirculation, and stagnation. Volumes of blood in the circuit begin coagulating when they become stagnant within the tube and/or connecting, leading to increased thrombosis formation.

Elimination of the low-shear areas, exposure steps, and zones or recirculation can reduce thrombosis formation. This includes reducing the inconsistencies created by connector edge expansions. Current connectors create a discontinuity on upstream, downstream, or both sides of a connector, which leads to thrombus formation. In contrast, this disclosure can reduce discontinuities in the stream and thus reduce thrombus formation in and around connectors. This disclosure includes connectors with continuous, smooth inner surfaces. By smoothing the transition from one tube to another through the connector, zones of stagnation are reduced, thereby reducing clotting.

Smoothing the transition from one flexible tubing segment to another may be accomplished by the use of a particularly shaped connector. A connector that prevents sharp diameter changes to ensure smooth surfaces can succeed at preventing clotting in the circuit. While traditional connectors expanded a flexible tube around the end of a connector, creating a diameter change and discontinuous surface, the connector of this disclosure is disposed around a flexible tubing segment. By allowing the outer diameter of a tube to match with the diameter of a connector bore, the flexible tubing fits firmly within the connector. Then, by allowing an inner lumen to have a smaller diameter equal to the inner diameter of a tube, the finished assembly will have inner surfaces that match the tubing segments on either side of the connector. This assembly may include tubing segments of different sizes such that the inner lumen of the connector can accommodate a transition from one inner diameter to another. The transition region remains smooth in its diameter change—ensuring a gradual difference, rather than a jump from one size to another. Thus, the connector prevents volumes of blood from being stagnant.

Various implementations include a connector for connecting flexible tubing segments. The connector includes a connector body having a first end and a second end disposed opposite one another along a longitudinal axis of the connector body. The connector body defines a first bore, a second bore, and a lumen. The first bore extends from the first end toward the second end. The first bore is configured for receiving an end portion of a first flexible tubing segment therein. The first bore has a circular cross-sectional shape and a first diameter. The second bore extends from the second end toward the first end. The second bore is configured for receiving an end portion of a second flexible tubing segment therein. The second bore has a circular cross-sectional shape and a second diameter. The lumen extends from the first bore to the second bore. The lumen has a circular cross-sectional shape and a third diameter that is less than each of the first diameter and the second diameter.

Various implementations include an assembly. The assembly includes a connector, a first flexible tubing segment, and a second flexible tubing segment. The connector includes a connector body having a first end and a second end disposed opposite one another along a longitudinal axis of the connector body. The connector body defines a first bore, a second bore, and a lumen. The first bore extends from the first end toward the second end. The first bore has a circular cross-sectional shape and a first diameter. The second bore extends from the second end toward the first end. The second bore has a circular cross-sectional shape and a second diameter. The lumen extends from the first bore to the second bore. The lumen has a circular cross-sectional shape and a third diameter that is less than each of the first and second diameter. The first flexible tubing segment includes a first end portion received within the first bore. The first flexible tubing segment has a first outer diameter and a first inner diameter. The first inner diameter is equal to a diameter of the lumen adjacent the first bore. The second flexible tubing segment includes a second end portion received within the second bore. The second flexible tubing segment has a second outer diameter and a second inner diameter. The second inner diameter is equal to a diameter of the lumen adjacent the second bore.

Figure 1B:
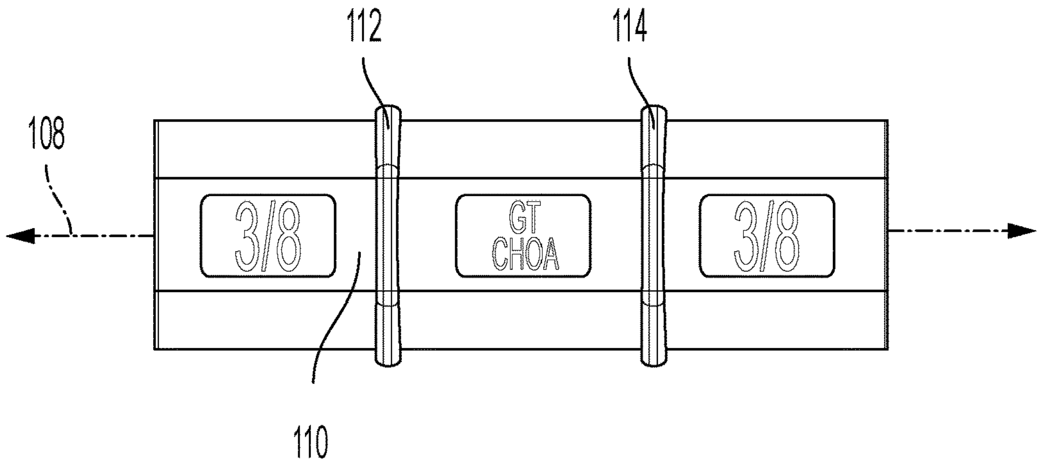
FIG. 1*b* shows a side view of a connector.
Figure 1C:
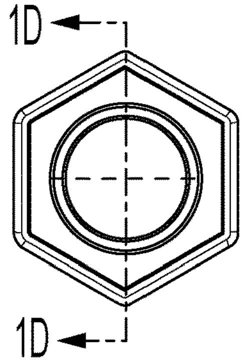
FIG. 1*c* shows a cross section of a connector.
Figure 1D:
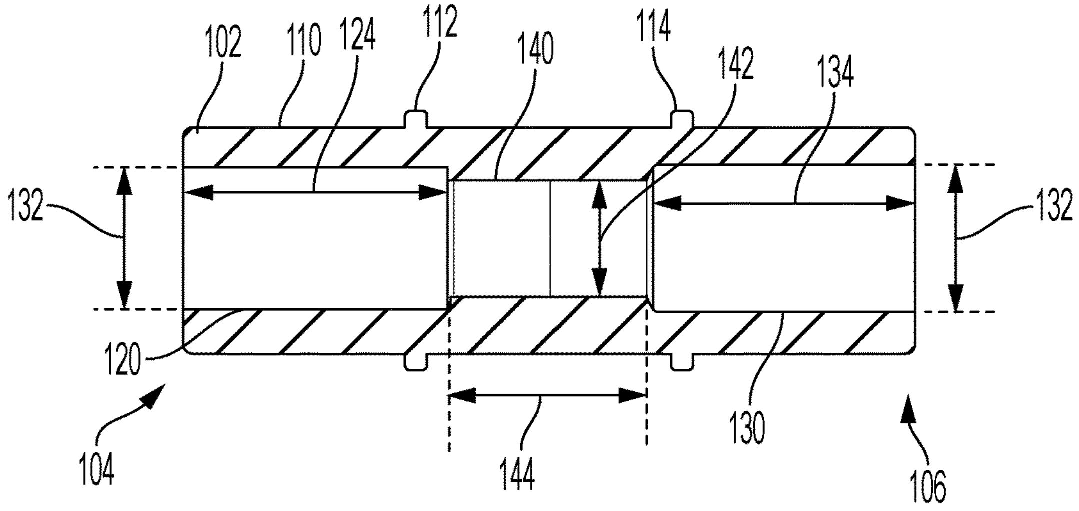
FIG. 1*d* shows a cross section of a connector along section A-A.

FIGS. 1*a*-1*d* show a connector 100 according to one implementation. The connector 100 was formed by injection molding and is made of polycarbonate. However, in other implementations, the connector may be formed by any other suitable method. In some implementations, the connector is made of any other suitable polymer or medical grade material.

The connector 100 includes a connector body 102, a first bore 120, a second bore 130, and a lumen 140. The connector body 102 has a first end 104 and a second end 106 disposed opposite one another along a longitudinal axis 108 of the connector body 102.

The first bore 120 extends from the first end 104 to the second end 106 along the longitudinal axis 108. The first bore 120 is configured for receiving an end portion of a first flexible tubing segment 191. The first bore 120 has a circular cross-sectional shape and a first diameter 122.

The second bore 130 extends from the second end 106 to the first end 104 along the longitudinal axis 108. The second bore 130 is configured for receiving an end portion of a second flexible tubing segment 192. The second bore 130 has a circular cross-sectional shape and a second diameter 132.

The lumen 140 extends from the first bore 120 to the second bore 130 along the longitudinal axis 108. The lumen 140 has a circular cross-sectional shape and a third diameter 142 that is less that each of the first diameter 122 and second diameter 132.

As shown in FIGS. 1*a*-1*d*, connector 100 may receive a first flexible tubing segment 191 with, for example, an inner diameter of ⅜ inches. Thus, the first bore 120 has a first diameter 122 that is larger than ⅜ inches to accommodate outer diameter of the first flexible tubing segment 191. Similarly, connector 100 may receive a second flexible tubing segment 192 with, for example, an inner diameter the same as that of the first flexible tubing segment 191. Thus, as shown in FIGS. 1*a*-1*d*, both first and second flexible tubing segments 191, 192 have an outer diameter equal to each other which are equal to both the first diameter 122 of the first bore 120 and the second diameter 132 of the second bore 130. The lumen 140 has a third diameter 142 equal to the inner diameter of the first and second flexible tubing segments 191, 192. As shown in FIGS. 1*a*-1*d*, the inner diameters of the first and second flexible tubing segments 191, 192 line up with the lumen 140 having a constant third diameter 142 equal ⅜ inches. The result is a smooth transition from first flexible tubing segment 191 to lumen 140 to second flexible tubing segment 192 along the longitudinal axis 108.

By allowing the outer diameter of a flexible tubing to match with the diameter of a connector bore, the flexible tubing fits firmly within the connector body 102. Then, by allowing an inner lumen 140 to have a smaller diameter equal to the inner diameter of a tube, the complete assembly will have inner surfaces that match the tubing segments on either side of the connector body 102. The transition region remains smooth in its diameter change—ensuring a gradual difference, rather than a jump from one size to another. Thus, the connector prevents volumes of blood from being stagnant, which causes clotting in the circuit.

The flexible tubing is fit within the connector body 102 by using cyanoacrylate glue placed between the outer surface of the flexible tubing and the inner surface of the connector body. However, in other implementations, the flexible tubing may be secured to the connector body by any other suitable means (e.g., pressure fit or medical tape). In some implementations, the connector and flexible tubing are manufactured as a single, pre-assembled unit rather than connected separately.

As shown in FIGS. 1*a*-1*d*, the cross-sectional shape of the connector body 102 is a hexagonal cross-sectional shape. The connector body 102 includes a plurality of external surfaces 110. In some implementations, the external surfaces 110 are planar surfaces. In some implementations, the connector body 102 has a non-circular cross-sectional shape defined by one or more external surfaces 110 of the connector body 102. In other implementations, the connector body 102 has a polygonal cross-sectional shape defined by a plurality of external surfaces 110. The cross-sectional shape of the connector body 102 provides grip for a user so that placing the connector and inserting the tubing segments is made easier. The cross-sectional shape provides grip stability in the radial direction about the longitudinal axis 108.

In the connector 100 of FIGS. 1*a*-1*d*, the connector body 102 includes ribs on the external surface 110. A first rib 112 is spaced apart from each of the first end 104 and second end 106. A second rib 114 is spaced apart from the first rib 112 and from each of the first end 104 and the second end 106. The ribs 112, 114 extend out from the external surface 110 perpendicular to the longitudinal axis 108. In FIGS. 1*a*-1*d*, the ribs 112, 114 form a ring extending around the longitudinal axis 108. In other implementations, the ribs 112, 114 extend only partially around the longitudinal axis 108, for example, only halfway or only a quarter of the way around. In other implementations, the ribs 112, 114 extend out from the external surface 110 at discrete points. In other implementations, the ribs 112, 114 extend out from the external surface 110 in sections around the longitudinal axis 108, for example, two rib sections disposed on opposite sides of the connector body 102 about the longitudinal axis 108.

The ribs 112, 114 on the external surface 110 provide grip for a user so that placing the connector and inserting the tubing segments is made easier. The ribs 112, 114 provide grip stability in the longitudinal direction along the longitudinal axis 108.

Although two ribs 112, 114 are shown in FIGS. 1*a*-1*d*, in other implementations, the connector body 102 includes a plurality of ribs 112, 114 each extending along one or more external surfaces 110 of the connector body 102. For example, in some implementations, there may be one rib, three ribs, four ribs, five ribs, six ribs, eight ribs, or ten ribs disposed along the external surface 110 of the connector body 102.

As shown in FIGS. 1*a*-1*d*, the first bore 120 has a first length 124 in the direction of the longitudinal axis 108. The second bore 130 has a second length 134 in the direction of the longitudinal axis 108. As shown in FIGS. 1*a*-1*d*, first length 124 is equal to second length 134. In other implementations, the first length 124 is different than the second length 134.

As shown in FIGS. 1*a*-1*d*, the lumen 104 has a third length 144 in the direction of the longitudinal axis 108. The third length 144 is less than each of the first length 124 and the second length 134. In other implementations, the third length 144 is greater than or the same as each of the first length 124 and the second length 134.

The first diameter 122 is constant along an entire length of the first bore 120 in the direction of the longitudinal axis 108, and the second diameter 132 is constant along an entire length of the second bore 130 in the direction of the longitudinal axis 108. In some implementations, the diameters may vary along the longitudinal axis 108.

Figure 2A:
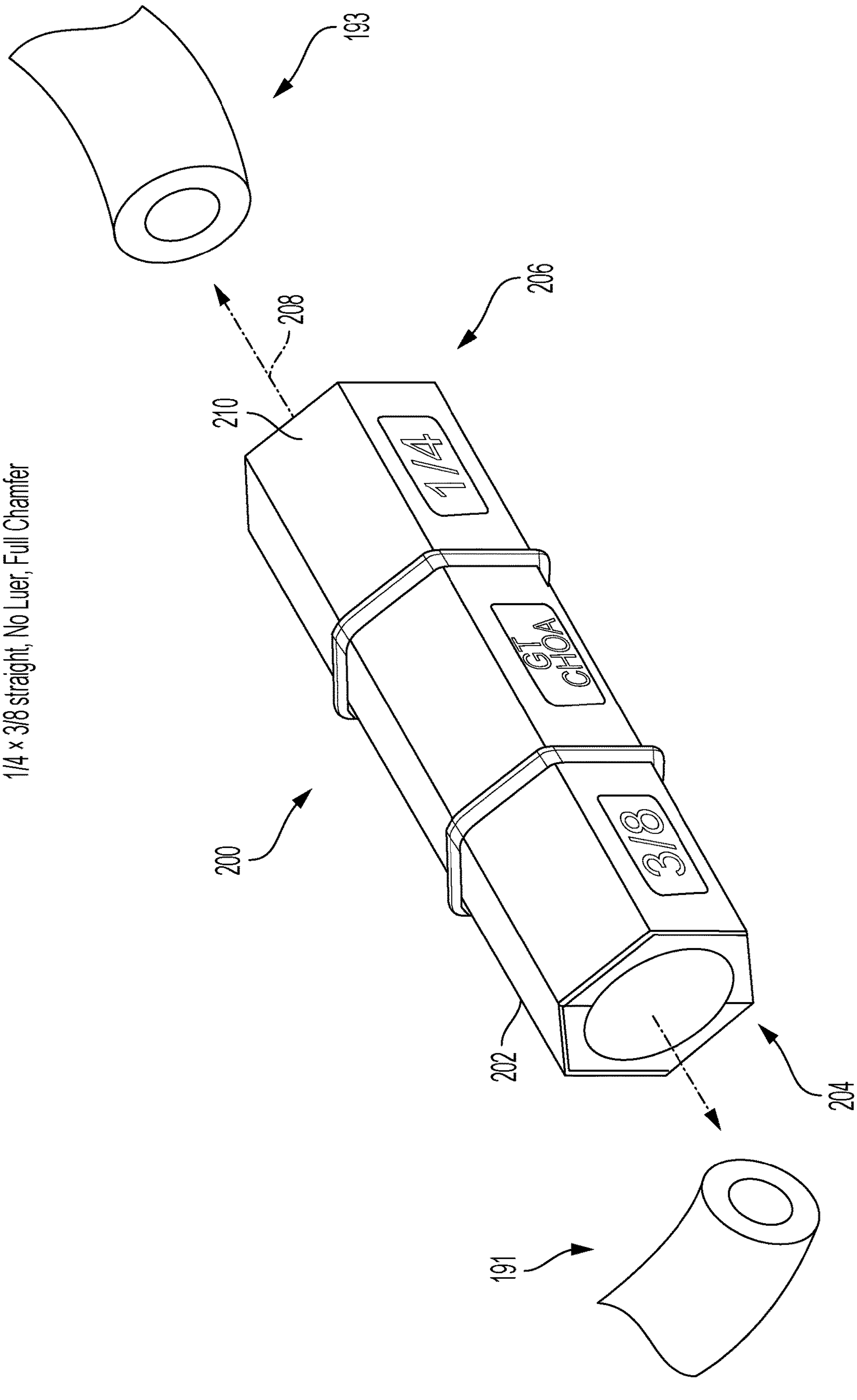
FIG. 2*a* shows a perspective view of a connector.
Figure 2B:
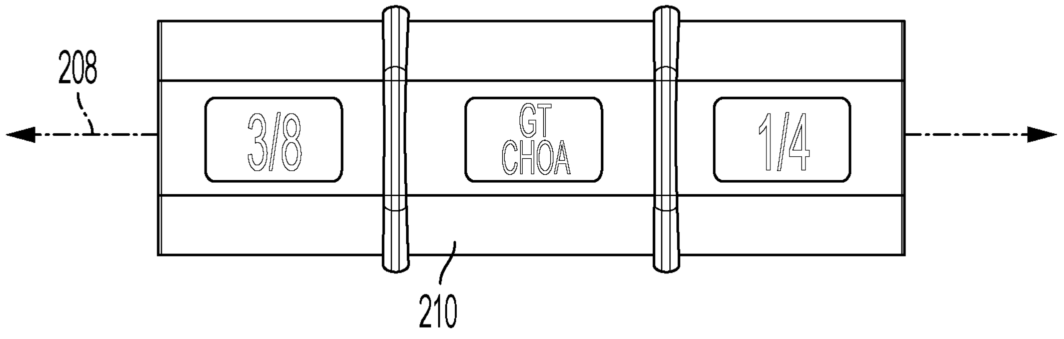
FIG. 2*b* shows a side view of a connector.
Figure 2C:
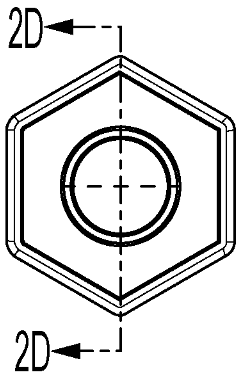
FIG. 2*c* shows a cross section of a connector.
Figure 2D:
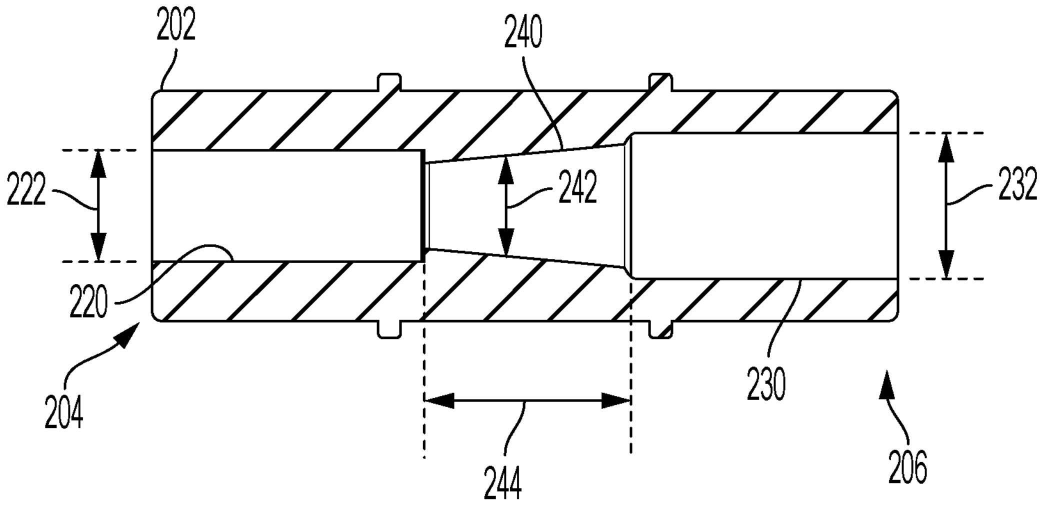
FIG. 2*d* shows a cross section of a connector along section A-A.

Although the first diameter 122 is equal to the second diameter 132 in FIGS. 1*a*-1*d*, in other implementations, the first diameter 122 is different than the second diameter 132. This assembly may include tubing segments of different sizes such that the inner lumen 140 of the connector 100 can accommodate a transition from one inner diameter to another. For example, FIGS. 2*a*-2*d* show a connector according to one implementation. FIGS. 2*a*-2*d* show a connector 200 including a connector body 202, an external surface 210, a first bore 220, a second bore 230, and a lumen 240. The connector body 202 has a first end 204 and a second end 206 disposed opposite one another along a longitudinal axis 208 of the connector body 202. The first bore 220 has a first diameter 222 and the second bore 230 has a second diameter 232. As shown in FIGS. 2*a*-2*d*, the first diameter 222 is smaller than second diameter 232.

Connector 200 may receive a first flexible tubing segment 191 with, for example, an inner diameter of ⅜ inches. Thus, the first bore 220 has a first diameter 122 that is larger than ⅜ inches to accommodate outer diameter of the first flexible tubing segment 191. In contrast to connector 100 of FIGS. 1*a*-1*d*, connector 200 may receive a larger flexible tubing segment on the second end 206 ("larger second flexible tubing segment" 193). Larger second flexible tubing segment 193, being one of two flexible tubing segments compatible with connector 200, has an inner diameter different from that of the first flexible tubing segment 191. For example, first flexible tubing segment 191 has an inner diameter of ⅜ inches while larger second flexible tubing segment 193 has an inner diameter of ¼ inches.

As shown in FIGS. 2*a*-2*d*, both first flexible tubing segment 191 has an outer diameter equal to the first diameter 222 of the first bore 220, while larger second flexible tubing segment 193 has an outer diameter equal to the second diameter 232 of the second bore 220.

Although the lumen 140 of FIGS. 1*a*-1*d* has a third diameter 142 that is constant along the entire length of the lumen 140 in the direction of the longitudinal axis 108, in other implementations, the third diameter 142 varies along at least a portion of the length of the lumen 140 in the direction of the longitudinal axis. For example, in FIGS. 2*a*-2*d*, the lumen 240 has a third diameter 242 which varies along the entire length (third length 244) of the lumen 240. The complete assembly will have inner surfaces that match the tubing segments on either side of the connector body 202. The transition region remains smooth in its diameter change—ensuring a gradual difference, rather than a jump from one size to another. Thus, the connector prevents volumes of blood from being stagnant, which causes clotting in the circuit.

The varying diameter of lumen 240 is configured such that the inner diameters of the two flexible tubing segments will line up with either end of the lumen 240 for a smooth transition through the connector 200. For example, first flexible tubing segment 191 includes an inner diameter of ⅜ inches which is equal to the diameter of the lumen 240 closer to the first end 204 abutting the first bore 220. The larger second tubing segment 193 includes an inner diameter of ¼ inches which is equal to the diameter of the lumen 240 closer to the second end 206 abutting the second bore 230. Thus, the lumen 240 of FIGS. 2*a*-2*d* is configured to receive two flexible tubing segments of different diameters and allow for smooth fluid flow through the connector 200 by use of a constantly varying third diameter 242.

While the third diameter 242 of the lumen 240 varies along an entire length of the lumen 240 in the direction of the longitudinal axis 208, in other implementations, the diameter varies along a portion of the length of the lumen 240.

Figure 3A:
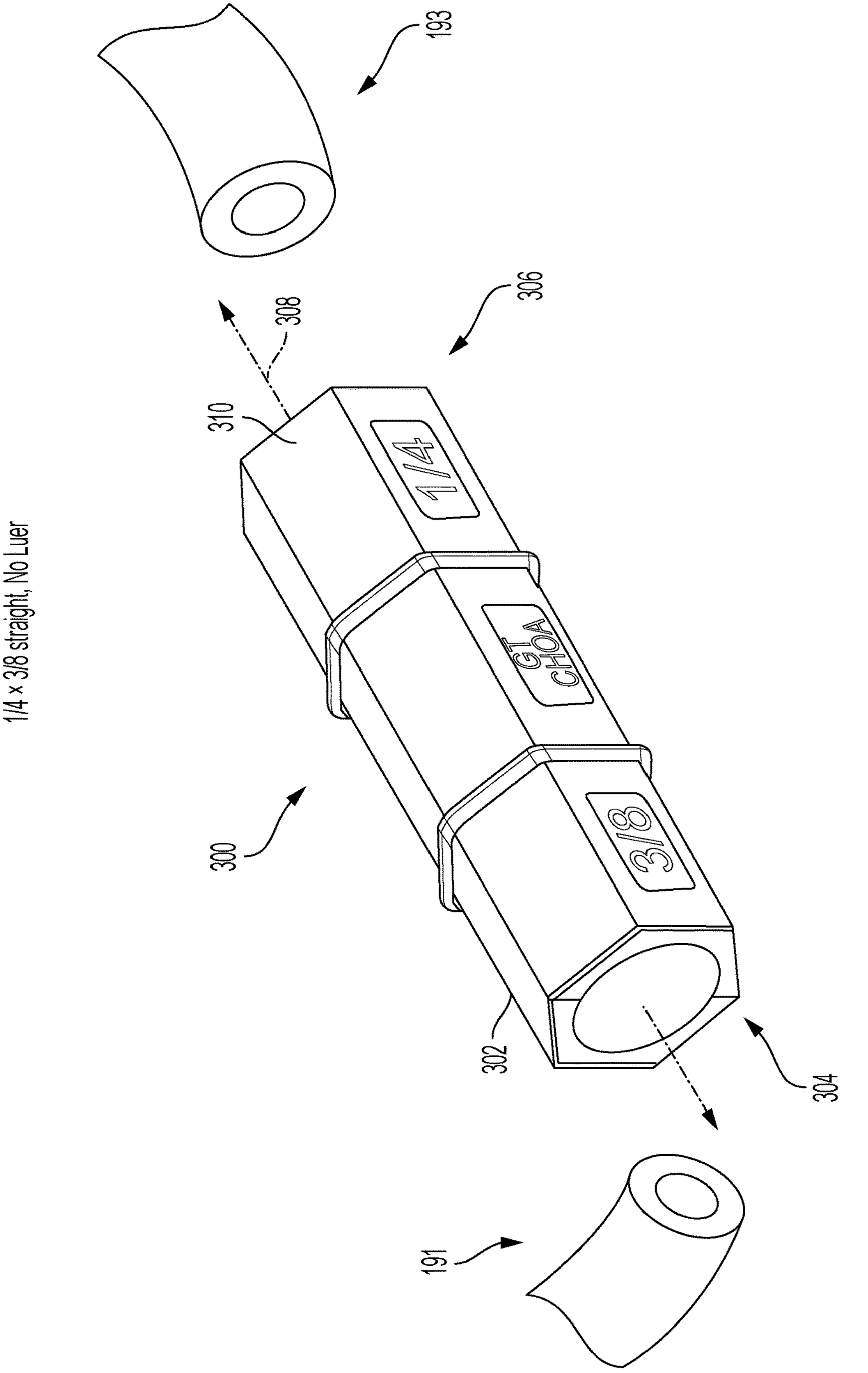
FIG. 3*a* shows a perspective view of a connector.
Figure 3B:
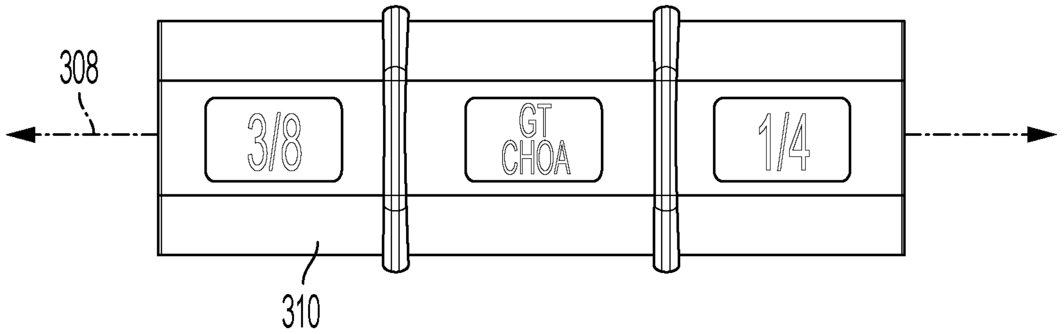
FIG. 3*b* shows a side view of a connector.
Figure 3C:
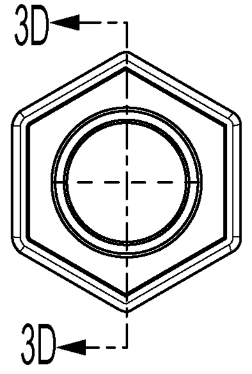
FIG. 3*c* shows a cross section of a connector.
Figure 3D:
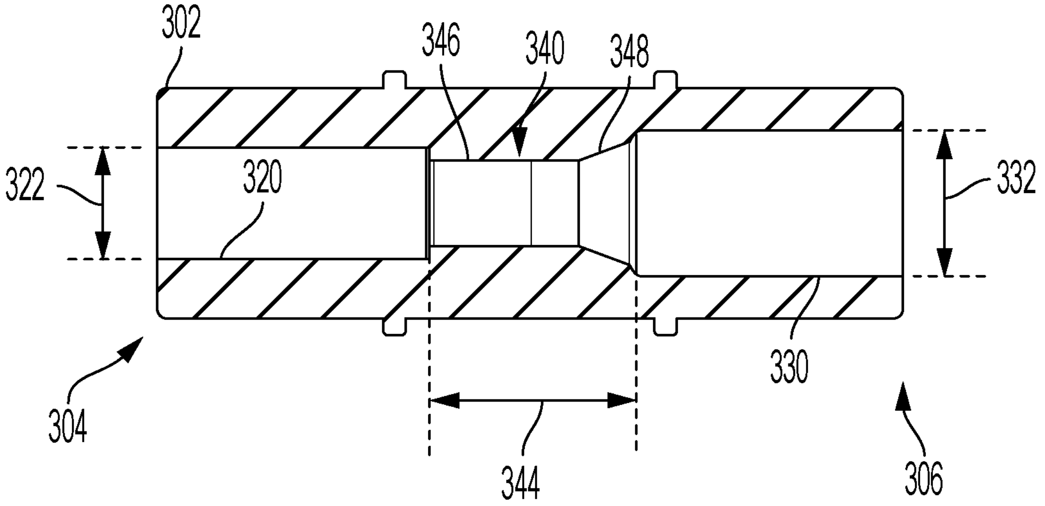
FIG. 3*d* shows a cross section of a connector along section A-A.

While the third diameter 242 of the lumen 240 varies in a linear manner in the direction of the longitudinal axis 208, in other implementations the diameter varies in a non-linear manner. For example, FIGS. 3*a*-3*d* show a connector 300 according to one implementation. FIGS. 3*a*-3*d* show a connector 300 including a connector body 302, an external surface 310, a first bore 320, a second bore 330, and a lumen 340. The connector body 302 has a first end 304 and a second end 306 disposed opposite one another along a longitudinal axis 308 of the connector body 302. The first bore 320 has a first diameter 322 and the second bore 330 has a second diameter 332. As shown in FIGS. 3*a*-3*d*, the first diameter 322 is smaller than second diameter 332.

Similar to FIGS. 2*a*-2*d*, the connector 300 of FIGS. 3*a*-3*d* is configured to receive a first flexible tubing segment 191 on the first end 304 and a larger second flexible tubing segment 193 on the second end 306.

The lumen 340 includes a first portion 346 extending from the first bore 320 and having a constant diameter. The lumen 340 also includes a second portion 348 extending from the first portion 346 to the second bore 330 and having a varying diameter in the direction of the longitudinal axis 308. As shown in FIGS. 3*a*-3*d*, the first portion 346 of the lumen 340 has a diameter equal to the inner diameter of the first flexible tubing segment 191, which is ⅜ inches. The second portion 348 of the lumen 340 has a varying diameter which terminates at a point abutting the second bore 330 such that the diameter of the second portion 348 is equal to the inner diameter of the larger second flexible tubing segment 193, which is ¼ inches. Thus, the lumen 340 of FIGS. 3*a*-3*d* is configured to receive two flexible tubing segments of different diameters and allow for smooth fluid flow through the connector 300 by use of both a constant diameter first portion 346 and a varying diameter second portion 348. The complete assembly will have inner surfaces that match the tubing segments on either side of the connector body 302. The transition region remains smooth in its diameter change—ensuring a gradual difference, rather than a jump from one size to another. Thus, the connector prevents volumes of blood from being stagnant, which causes clotting in the circuit.

While the second portion 348 varies diameter in a linear manner in the direction of the longitudinal axis 308, in other implementations, the second portion 348 may vary diameter in a non-linear manner, as shown across the entire length of lumen 340 including both portions 346, 348. In other implementations, the non-linear diameter variations may include a curved portion of the lumen.

Figure 4A:
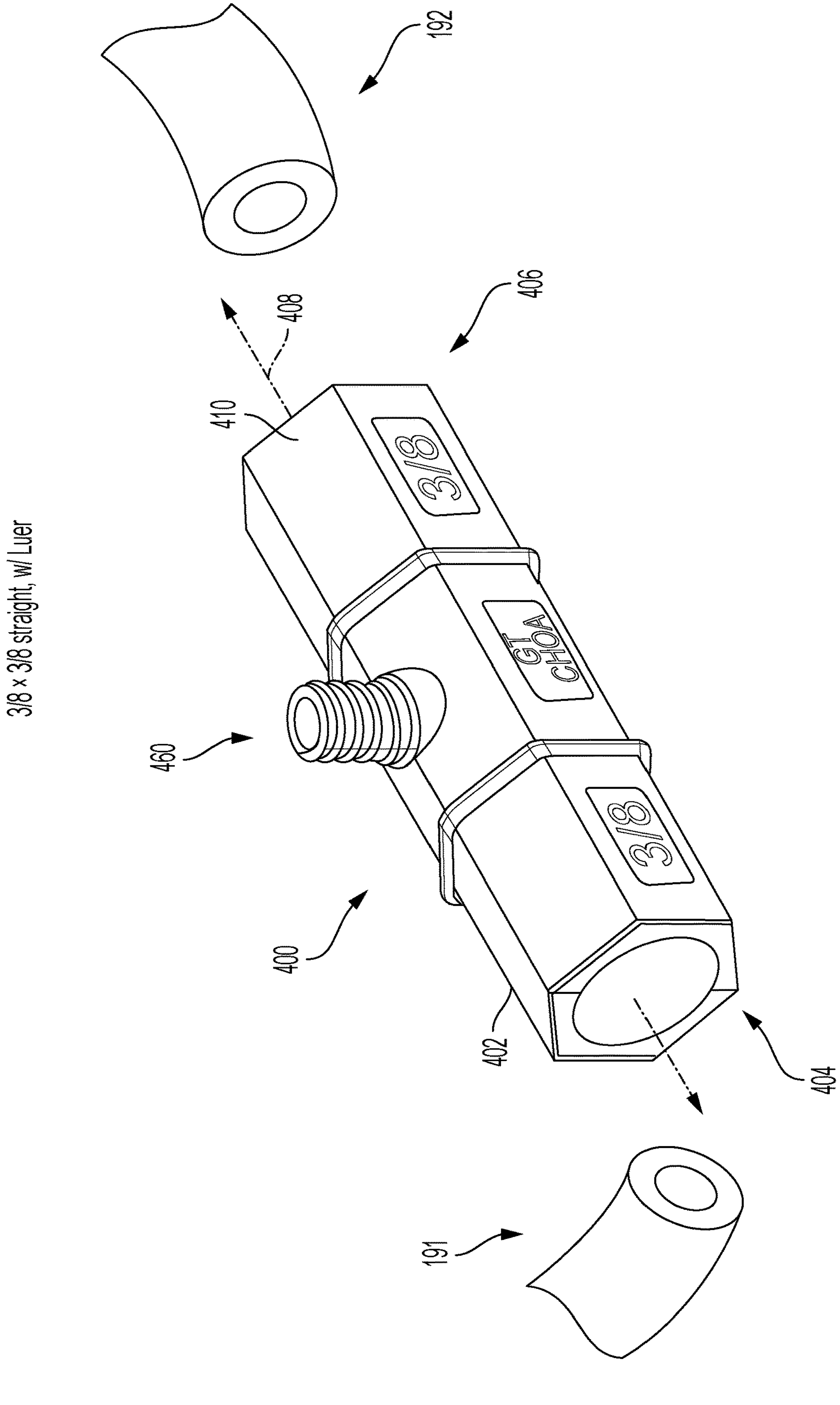
FIG. 4*a* shows a perspective view of a connector.
Figure 4B:
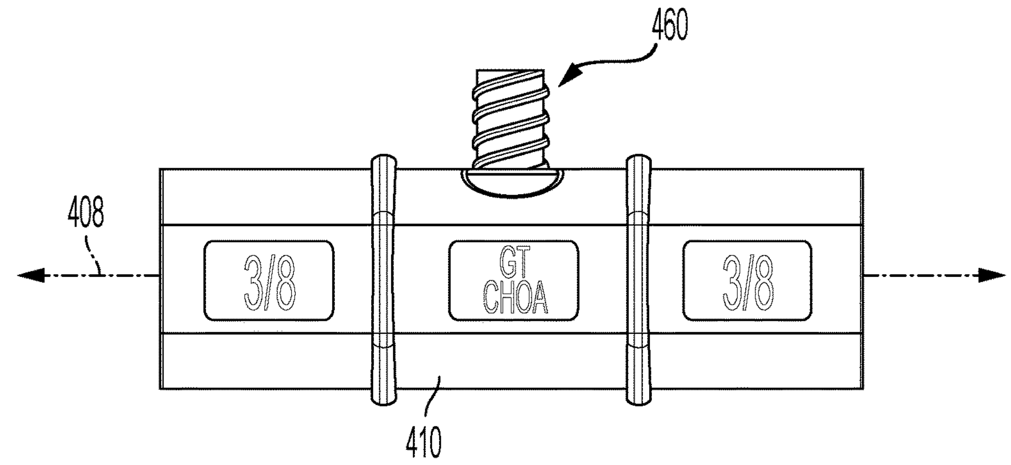
FIG. 4*b* shows a side view of a connector.
Figure 4C:
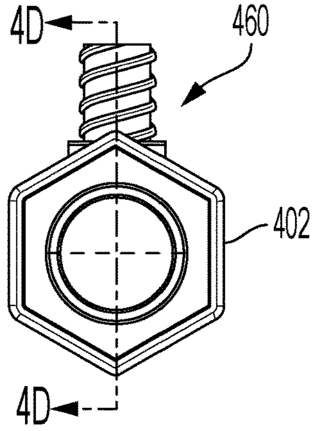
FIG. 4*c* shows a cross section of a connector.
Figure 4D:
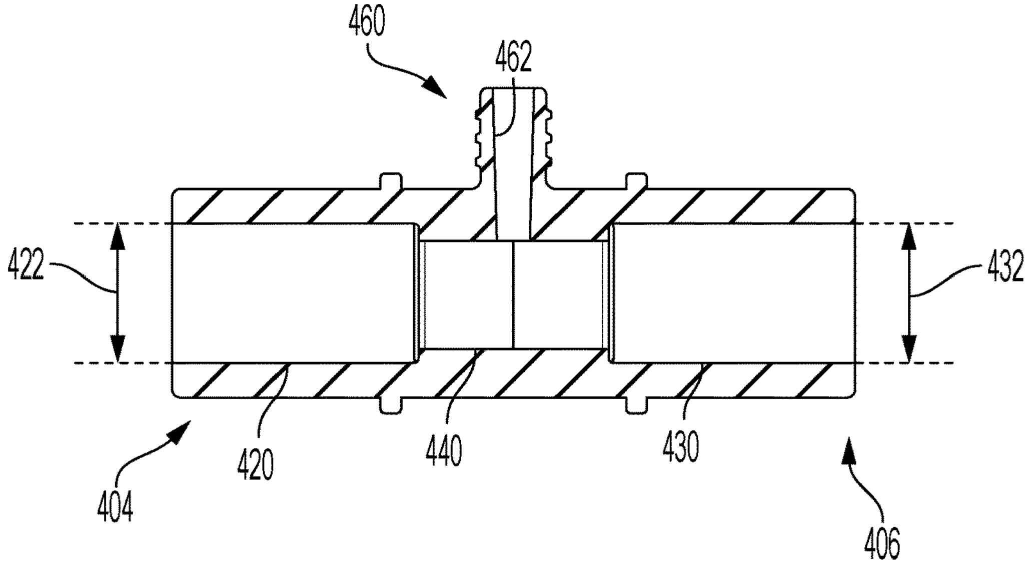
FIG. 4*d* shows a cross section of a connector along section A-A.

In various implementations, the connector further includes a luer body configured for removably coupling with a mating luer adapter. Such a luer adapter may solve clinical challenges related to having a port for drug infusion or for access to fluid, for example access to blood within the flexible tubing and/or connector. For example, FIGS. 4*a*-4*d* show a connector 400 according to one implementation.

FIGS. 4*a*-4*d* show a connector 400 including a connector body 402, an external surface 410, a first bore 420, a second bore 430, a lumen 440, and a luer body 460. The connector body 402 has a first end 404 and a second end 406 disposed opposite one another along a longitudinal axis 408 of the connector body 402. The first bore 420 has a first diameter 422 and the second bore 430 has a second diameter 432. As shown in FIGS. 4*a*-4*d*, the first diameter 422 is the same as the second diameter 432. As shown in FIGS. 4*a*-4*d*, the lumen 440 has a constant third diameter 442 along the entire length of the lumen 440, similar to that of FIGS. 1*a*-1*d*. The complete assembly will have inner surfaces that match the tubing segments on either side of the connector body 402. The transition region remains smooth in its diameter change—ensuring a gradual difference, rather than a jump from one size to another. Thus, the connector prevents volumes of blood from being stagnant, which causes clotting in the circuit.

The luer body 460 is coupled to the connector body 402 and extends perpendicular to the longitudinal axis 408. The luer body 460 defines a second lumen 462 in fluid communication with the lumen 440 of the connector body 402. The luer body 460 is centered between the first end 404 and the second end 406. The connector body 402 and the luer body 460 are integrally formed with one another.

In some implementations, the luer body 460 may not be centered between the first end 404 and second end 406 but may be disposed off-center to the connector body 402. In some implementations, the connector may include a plurality of luer bodies 460 in fluid communication with the lumen 440, for example, two or three luer bodies spaced apart from one another along the longitudinal axis 408 and/or radially around the longitudinal axis 408.

Experimental Section 1

Collection and Analysis of Examples of Thrombus Formation in Current Clinical Devices 3.1 Extracorporeal Membrane Oxygenation (ECMO) Circuits 3.1.1 Background The use of extracorporeal membrane oxygenation (ECMO) as a form of extracorporeal life support (ECLS) is now a well-established therapy for cardiorespiratory failure. Currently the use of ECLS is dominated by neonatal and pediatric patients over adult patients, and use of ECLS is increasing for both adults and pediatric patients. The ELSO registry currently documents use of ECMO in >55,886 pediatric and neonatal patients since 1990. Neonatal patients (<30 days old) account for 47% of all ECLS cases, pediatric patients (30 days-16 years old) account for 24% of total cases, and adult patients account for the remaining 29%. However, in the face of ever-increasing experience, there continues to be significant morbidity and mortality related to clotting and bleeding related complications, especially in the neonatal and pediatric population. Overall hospital to discharge survival of ECLS cases is 58% for adults, and 41% for both children and neonates. In addition to the events captured on the patient side, issues related to clotting contribute significantly to equipment malfunctioning necessitating interventions such as circuit and oxygenator changes. For respiratory ECLS patients, adverse events relating to mechanical malfunctions, bleeding, and infarction occurred in 40.4%, 62.4%, and 46.3% of neonate, pediatric, and adult patients respectively. The incidence of these events was higher in cardiac patients, and occurred in 67.5%, 69.1%, and 62.4% of neonate, pediatric and adult patients respectively. In the neonatal and pediatric population, management and appropriate balancing of the anticoagulation to counteract clotting is a tremendous challenge. A reduction in the inherent generation of clots in an ECMO circuit would reduce the need for anticoagulation with its concomitant bleeding complications. The goals of this study were to characterize clot formation and location within the circuit, to understand the basic histologic composition of the clot, and to ascertain the relation between clot location and the local hemodynamic conditions in the extracorporeal circuit.

3.1.2 Methods

ECMO Circuits were prospectively collected. Every patient supported with ECMO during this period was considered eligible for inclusion in the study. No circuits were excluded based on patient or ECMO characteristics and the study population was representative of the overall ECMO supported group in terms of age, diagnosis, type of ECMO and duration of ECMO. During the ECMO support, all patients were managed by using the institutional protocol for anticoagulation and blood product administration. The anticoagulation is achieved using unfractionated heparin, with target anti-Xa levels between 0.3 to 0.7 as well as bedside activated clotting time (ACT) measurements using an i-STAT device with a Kaolin ACT cartridge. The ACT target ranges were adjusted based on patient anti-Xa levels as well as clinical scenario of bleeding or clotting problems. Blood component therapies were administered as needed to maintain hematocrit between 35% and 45%, platelet count of greater than 100,000/cmm, and fibrinogen count of greater than 200 mg/dl.

Following removal of a patient from ECMO support, the circuits were immediately drained of blood and gently flushed and filled with normal saline. The circuits were refrigerated (4 C) 24-48 hours until inspection. Each circuit was inspected for gross clots easily visible through the saline. The location of adhered clots was recorded, and regions of interest were photographed. To determine if clots were adherent, saline was perfused lightly in the direction of flow. A clot was deemed adherent if it remained completely or partially attached during perfusion. Tubing sections of interest were cut from the circuit, then labeled and photographed. Clots were then excised from the sections and were immediately fixed in 10% formalin until histological analysis. Oxygenator clots were removed by either flushing clots out of the oxygenator with saline or with forceps if a sample was in reach of the entry. Patient parameters of interest while on ECMO were also collected.

A single connector has two tubing-connector junctions (TCJs), one upstream and one downstream, and the TCJ was cataloged according to its internal diameter. A typical expansion connector, for example, would have one ¼ inch TCJ upstream and one ⅜ inch TCJ downstream. The TCJ is formed by the thickness of the connector wall and the region of tubing that is expanded to fit over the outer diameter of the connector until it returns to the relaxed diameter. Clots were found in the step right at the junction in the lumen expansion zone on both the inlet and outlet ends of the connectors.

Histological Analysis: The dissected clots were embedded in paraffin and 5-micron thick slices were cut using a microtome. The slices were then mounted on glass slides and dried. Prior to staining, the slides were first deparaffinized and rehydrated. Carstairs stain for fibrin and platelets was used for staining. After staining, the slides were dehydrated via ethanol, cleared via xylene, and mounted. The Carstairs method stains platelets grey blue to navy, fibrin red, muscle bright red, collagen bright blue, and red blood cells yellow to clear. Images of the slides of the stained clots were analyzed using a pixel count by color in Adobe Photoshop CC 2015 in order to quantify the clot composition.

Computational Analysis: In order to identify the regions of extreme shear rate, flow separation, and other flow profiles of interest, computational fluid mechanics was used to analyze the flow through a segment of tubing with a connector. The tubing connector junction geometry was represented as a 2-D, axisymmetric cylinder in COMSOL Multiphysics. Representative ECMO flow rates (300 mL/min-5000 mL/min, Re=500 1014) were used to generate streamlines, velocity profiles, and shear rate profiles. The mesh is smaller at the boundary layer and expands in size in the lumen. The mesh contains 49,923 elements and has an area of 33,940 mm2. The dynamic whole blood viscosity was assumed to be 0.0004 Pa*s. Convergence was calculated with relative tolerance of 0.001.

Statistical Analysis: An unpaired Students t-test was used for significant differences among TCJ clotting incidences ($p<0.05$).

3.1.3 Results

Circuit Analysis: Visual documentation of gross clots was performed for all circuit components. Overall, 94% of circuits exhibited thrombus formation. Clots were not evenly distributed within the various components of the ECMO circuit. Although the tubing accounts for over 90% of the of the surface area exposed to blood, no clots were present on the free tubing surface. Instead, thrombi were focused at two locations: the tubing-connector junctions (TCJs) and the oxygenator.

The clots found at the TCJs were adherent and typically axisymmetric. The clots that were found in the oxygenator were not adherent to the membrane and were found loose on the deoxygenated or pre-membrane side. In some cases, clots from TCJs grew downstream and formed large masses greater than 2 cm2. The clots were only adherent to the TCJ attachment point, and under perfusion, the portion downstream of the TCJ was mobile. It is likely that these large clots would eventually break off and migrate to the oxygenator.

The ECMO circuits were comprised of approximately 5 m of tubing, with 6-12 connectors that were used to control flow and insert devices (oxygenator, filters, vascular access, etc.). Depending on the entry size of the circuit components, circuits were either a single diameter throughout or sized up and down between two diameters. Overall, the connectors accounted for about 10% of the exposed surface area yet exhibited 99% of the clots. The majority of ECMO circuit tubing diameter was ¼ inch (0.635 cm), and a typical circuit sized up and down between ¼ in and ⅜ in (0.953 cm) tubing. A few larger roller pump circuits sized up and down between ⅜ in and ½ in (1.27 cm) tubing, which accounted for only 8% of the circuits in this study.

The incidence of clotting was high at certain connectors and regions of the ECMO circuit and is correlated with areas of low shear ($p<<0.05$). The downstream end of expansion connectors was the most thrombogenic region in the ECMO circuits, with a 74% incidence rate, while its upstream counterpart had a thrombi incidence rate of only 13%. The ⅜ in diameter TCJs in general had a higher incidence of thrombosis of 45% overall vs. the ¼ in TCJs which were at 22%. In general, a downstream TCJ was significantly more likely to be thrombogenic than its upstream counterpart (33% vs 25.2%, $p=0.00297$).

Clot Histology: Histological analysis revealed the TCJ clots to be fibrin-rich and full of red blood cells (RBC). The oxygenator clots were coiled, and when expanded reached a length of ~5 cm. Oxygenator clots were present on the upstream pre-membrane side, and these clots were non-adherent. Under light perfusion of water, the clots dislodged and became mobile. With changes in oxygenator orientation (tipping), clots would slide in the direction of gravity. The composition of oxygenator clots is similar to the axisymmetric TCJ clots. The clots were on average 54% fibrin, 45% RBCs, and approximately 1% platelets. These red clots had a paucity of platelets.

Computational Fluid Dynamics Analysis: Based on the frequency distribution for the localization of adherent clots, the TCJ was identified as the highest priority site for potentiation of thrombosis. The hemodynamics of the TCJ zones was then characterized. CFD analysis of the TCJ region revealed distinct regions of low shear and a recirculation region on the downstream side of the TCJ. For the inlet to the connector, a zone of very low shear rates less than 50 s-1 is present in the corner. At the outlet, the zone of very low shear rates is even larger and directly located in the corner of the junction. Note that the shear rates outside of the corners return to a normal shear rate range from 450-1000 s-1. Thus, the clots co-locate directly at the site where blood is virtually stagnant with shear rates less than 50 s-1, or a shear stress of less than 0.2 Pa ($p<<0.05$).

3.1.4 Discussion

This is one of the first studies to examine in detail the location and histologic composition of thrombosis within the ECMO circuit. The analysis was extended to examine the statistical relationship of thrombosis with hemodynamics in the clinical circuits.

Analyses of clinical ECMO circuits revealed that thrombosis occurs consistently in nearly all of ECMO circuits at specific sites. The ECLS Registry collects information on clot formation at certain ECMO circuit components, however clots are typically recorded when large enough to be seen from outside the circuit while blood is still flowing, or when large enough to be detrimental. There is some variation in frequencies of these clot related complications. For example, in neonatal cardiac ECMO patients, 11.6% reported oxygenator clots, 3.9% reported bridge clots, 5.9% reported bladder clots, 4.3% reported hemofilter clots while 13.6% reported clots at other locations. For pediatric cardiac ECMO patients, the frequencies were as follows: oxygenator 8.4%, bridge 3.0%, bladder 4.0%, hemofilter 3.5% and other locations 10.2% reported clots. However, the ECMO circuits vary from facility to facility and the methods for recording clots are inconsistent. The development of a consistent method for identifying and reporting clots at specific sites in ECMO circuits would be of benefit to the patient population. In general, the data suggests that there is significant under-recognition and therefore under-reporting of circuit thrombosis.

The blood clots are found at specific locations within the circuit, primarily at the junctions made by the tubing and connectors (TCJs). It is noteworthy that although the tubing of the circuit constitutes a large portion of the surface area, there were no clots detected on the tubing surface. This is remarkable given that the standard circuit tubing (Class VI) is not coated. This TCJ clot location corresponds directly to zones of very low shear rates less than 50 s-1. Conversely, almost no clotting occurs with tubing material where shear rates are greater than 450 s-1 ($p<<0.05$) based on the CFD analysis. These conditions correspond to a Virchows Triad requirements for foreign surface, blood coagulation proteins, and zones of virtually stagnant blood. The areas of TCJs with shear rates<50 s-1 exhibited with high fibrin deposition and clot formation. The contribution of the local hemodynamics to local clot formation within the clinical ECMO system is critical.

Growing clots with small attachment points at TCJs are particularly worrisome, as they imply the possibility of large emboli which could cause devastating patient complications. These large clots would be subject to large drag forces and may be the source of the large, loose thrombi seen in the oxygenator.

The histologic appearance of clots in the ECMO circuits were fibrin-rich with few platelets. Thus, fibrin coagulation is the dominant problem for ECMO circuits rather than platelet thrombosis. The observation that ECMO clots are fibrin-rich is also consistent with reports of fibrinogen consumption in these patients. These red clots form in the setting of adequate anticoagulation with heparin and with therapeutic ACTs, illustrating the criticality of shear rate as a new factor. Currently, there are no universally established guidelines for ECMO anticoagulation, though unfractionated heparin is used at most ECMO centers, and very few centers (6 in a recent 119 center survey) use antiplatelet agents (acetylsalicylic acid, prostacyclin). Unfractionated heparin is effective at binding with antithrombin III (AT III) and causing a conformational change that leads to acceleration of AT III mediated inactivation of various coagulation factors including thrombin, factors IX, X, and XI. However, one of the major limitations of heparin in the setting of biomaterials is its inability to inactivate thrombin bound to fibrin or to biomaterial surfaces. Hence, it could be speculated that once fibrin deposition is initiated within the circuit, further propagation at low shear rate zones may not be sufficiently prevented by heparin use.

The data also indicate that circuits with centrifugal pumps have more incidence of thrombus than the roller pumps. The circuit thrombi may be due to the size of tubing to fit the centrifugal pump, which typically sizes up and down between diameters to go through the pump and the oxygenator. The data show these connectors of diameter increase and subsequent larger diameter regions to be highly thrombotic. Redesign of the circuit to avoid such step size changes may reduce the thrombogenicity of the circuit by reducing the number of regions with extreme low shear rates. Indeed, elimination of just 4 TCJs could reduce circuit thrombus by 80%.

The results demonstrate that the local hemodynamics, which create small zones of low shear rate, are strongly related to thrombus formation in extracorporeal circuits. It is recommended that circuits be designed to reduce the zones of low shear rate (<100 s-1) such as occurs at expansions and connectors. However, it is also still important to circuit design to exclude pathologically high shear rates that may induce hemolysis (>40,000 s-1) and/or platelet thrombosis (>10,000 s-1). The data also suggest that on the basis on thrombogenicity, roller pumps appear to produce less thrombosis than centrifugal pumps. Blood clotting in ECMO circuits may be reduced through an understanding of the induction of coagulation combined with fluid mechanic design to eliminate zones of stagnation.

Experimental Section 2

Novel Tubing Connectors Reduce ECMO Circuit Thrombosis

Background: Extracorporeal Membrane Oxygenation (ECMO) is used to treat over 19,000 patients each year with pulmonary failure. Historically ECMO has been predominately used in neonatal and pediatric populations, and in the recent years, cases of adult ECMO have been on the rise as it is used to treat acute respiratory distress syndrome (ARDS). This adult population has also increased due to respiratory problems associated with COVID-19.

In ECMO, issues with thrombosis and bleeding are the most common complications.3 Besides potentially causing ischemic events, thrombotic complications include oxygenator and pump malfunctions that require the circuit to be replaced. Thrombotic risks are mitigated through treatment with anti-coagulants, typically heparin, but this treatment comes with the associated risks of increased bleeding. Balancing the risks of thrombosis and bleeding is difficult.

Inspection of over 100 clinical ECMO circuits reveals that 80% of clots form at the tubing-connector junctions. These junctions create a geometric sudden contraction or expansion region where there is a mismatch between tubing and connector inner diameters (IDs). The hypothesis is that by eliminating the step changes in diameter, clot formation in tubing connectors will be eliminated. A novel connector was designed where the ID of the two components is matched. This matching of diameter should eliminate the dead zone from traditional connectors and result in less thrombosis. To test this hypothesis, an in vitro circuit was developed using porcine whole blood containing both traditional and novel tubing connectors run for 96 hours. The traditional and novel connectors were tested in 4 caprine ECMO loops run for up to 48 hours. The endpoints of thrombus appearance and protrusion demonstrated superiority of the novel connectors in reducing in circuit thrombosis.

Methods: Connectors were designed to be compatible with standard ⅜" tubing. After creating a CAD model of the connector, it was sent to an injection molding company specializing in medical devices. An aluminum mold for the part was created and the connector was injection molded using Chi Mei Wonderlite Polycarbonate PC-110U. These parts were tested to confirm that the inner diameter of the connector remained flush with the inner diameter of the ⅜" tubing.

Tubing used with the novel connector is cut using a pipe cutter to ensure that a flat, perpendicular surface is created which can sit flush on the shelf of the novel connector. To prevent the tube from coming out during the experiment, cyanoacrylate glue was placed between the tubing and the connector and allowed to cure. This method was shown to be able to withstand tensile forces of ~10 lbs (Data not shown).

In Vitro: Porcine blood for in vitro testing was collected from a local abattoir. Fresh whole blood was added to 1 L bottles (Nalgene) containing sufficient Sodium Heparin (Fisher Scientific) solution to bring the final concentration to 3.5 IU/mL. For the in vitro circuits, 3 traditional connector and 3 new connectors were placed in an alternating arrangement in a 2 m long loop of ⅜" tubing. A flow rate of 0.5 L/m was achieved using a roller pump (Cobe). At 48 hrs the loop is drained and the blood is replaced with fresh blood from a second pig. For the duration of the experiment, half of the loop is submerged in a water bath set to 37 C which maintained the blood at physiologic temperature. At T=0 and T=48 hrs 0.8 mg/mL glucose (Sigma-Aldrich), 0.28 mg/mL L-glutamine (Sigma-Aldrich) and 0.01% v/v anti-biotic/anti-mycotic (Gibco) are added to blood to keep the cells viable for 48 hrs. Every 12 hours 3.5 U/mL heparin is added to the blood. Circuits were run for 96 hrs, then carefully disassembled and the entire tubing and connectors were visually inspected for clot presence.

In Vivo: To determine if the novel connectors would improve clot load in an in vivo setting, a caprine model of arterio-venous ECMO was developed. The 4 goats used for this model were Capra Aegagrus Hircus goats with weights ranging from 30 to 45 kg. The procedures were approved by T3 IACUC protocol DW13G. Custom packed ECMO circuits were modified to incorporate the novel connector. New connectors were placed in three locations: upstream of the pump, between the pump and oxygenator and downstream of the oxygenator. In each instance, the new connector was situated nearby a traditional connector which acted as a paired control. Each goat underwent surgical placement of carotid arterial and jugular venous cannulas. The goats were placed under general anesthesia with endotracheal intubation and monitored by a veterinary anesthetist during the operations.

Clots were graded using two separate qualitative scales: visualization of the clot presence from the outside the connector; and a measure of how much the clot protruded into the lumen: Lumen Protrusion Grade. The grading scales are described as follows—Clot Presence: 0=No Clot; 1=Minimal Clot Contained to Separation Region; 2=Clot Within Separation Region; 3=Clot Significantly Extending into Lumen—Lumen Protrusion Grade: 0=No Clot; 1=Surface Clot; 2=Clot Extends into Flow; 3=Clot Extends into Flow, Partially Detached from Wall.

Results: The novel connector eliminates the recirculation region found at the tubing-connector junction as shown previously. The elimination of stagnant flow zones was confirmed in the injection molded part. The connector was molded from a clear resin to allow for visualization of any thrombi that might form. Tolerances of the connector inner diameter surround the tubing were tested to create a component where the tubing fit snuggly into the connector without deforming the inner diameter of the tubing.

In vitro flow loop: Three novel and three traditional connectors were tested in a loop of ⅜" tubing with blood perfused at a flow rate of 0.5 L/min. Following perfusion with porcine blood for 96 hrs, all the traditional connectors had at least one clot present, with an average of 1.3 clots per connector. In contrast, only 1 of the 9 novel connectors had a small visible thrombosis at the tubing-connector junction. Clots in the traditional connectors were red in appearance and located at the junction of the connector and tubing on both the upstream and downstream ends. No such clots were present at the connector-tubing junction for the novel connectors.

In vivo: Over 60% of the traditional connectors had large thrombi extending into the lumen. In contrast, nearly 60% of novel connectors had either no visible clots or a minimal film of blood remaining after flushing which was not contiguous with the lumen (i.e. caught between the outside of the tubing and the connector). The other 40% of novel connectors had small clots in the gap between the cut edge of the tubing and the connector. These clots did not extend into the lumen.

To grade the severity of clots present, the Lumen Protrusion Grade was used. Traditional connectors again had a significantly higher grade than the novel connectors (Fisher's Exact Test, $p<0.0001$). The median score for traditional connectors was Grade 2 and the median score for novel connectors was Grade 0. Nearly all traditional connectors had clots visibly in the lumen of the tubing and over 20% of those were partially detached from the surface of the tubing-connector junction. These represent clots that could grow beyond the limits of the separation region or break and embolize to the pump, oxygenator or patient. The vast majority of novel connectors had no clot visible when looking down the lumen of the tubing.

Discussion: The novel connector can reduce clot formation in both in vitro and in vivo ECMO circuits. While other studies have focused on modifying surface chemistries to prevent thrombosis, this case study highlights how geometric modifications can improve the local fluid mechanics of blood and result in significant improvements in thrombosis formation. In this case, by removing a step change in the lumen, the connector can eliminate thrombosis formation at the tubing-connector junction, a site previously identified as accounting for 80% of clots in ECMO circuits.

A strong reduction in circuit thrombosis may lead to less need for anti-coagulation in ECMO patients and a reduction in occlusive or ischemic complications. The clinical minute-to-minute management of the patients may be reduced if heparin needs are reduced, with a large improvement in time management. In addition to the straight connector presented above, connectors can be made that eliminate the tubing-connector junction step while joining tubing with disparate IDs or providing luer-lock access points.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device are disclosed herein, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. A connector for connecting flexible tubing segments, the connector comprising:

a connector body having a first end defining a first opening and a second end defining a second opening disposed opposite one another along a linear longitudinal axis of the connector body, the connector body defining:

a first bore extending from the first end toward the second end and configured for receiving an end portion of a first flexible tubing segment therein, the first bore having a circular cross-sectional shape and a first diameter;

a second bore extending from the second end toward the first end and configured for receiving an end portion of a second flexible tubing segment therein, the second bore having a circular cross-sectional shape and a second diameter;

a lumen extending from the first bore to the second bore, the lumen having a circular cross-sectional shape and a third diameter that is less than each of the first diameter and the second diameter, wherein the first bore, the second bore, and the lumen are coaxial with the linear longitudinal axis; and a luer body configured for removably coupling with a mating luer adapter, wherein the luer body is coupled to the connector body and extends perpendicular to the linear longitudinal axis, the luer body defining a second lumen in fluid communication with the lumen of the connector body, wherein the connector body has a hexagonal cross-sectional shape defined by one or more external surfaces, the connector body further comprising a plurality of ribs each extending outwardly from the one or more external surfaces, and wherein the connector body is sized such that when the first flexible tubing segment is inserted into the first bore via the first opening and the second flexible tubing segment is inserted into the second bore via the second opening, a smooth flow path from the first flexible tubing segment, through the lumen, and to the second flexible tubing segment is formed, the flow path minimizing zones of stagnation, recirculation, and low shear rate of a fluid flowing therein.

2. The connector of claim 1, wherein the first bore has a first length in the direction of the longitudinal axis, wherein the second bore has a second length in the direction of the longitudinal axis, wherein the first length is equal to the second length, and wherein the lumen has a third length in the direction of the longitudinal axis, and wherein the third length is less than each of the first length and the second length.

3. The connector of claim 1, wherein the first diameter is constant along an entire length of the first bore in the direction of the longitudinal axis, and wherein the second diameter is constant along an entire length of the second bore in the direction of the longitudinal axis, and wherein the third diameter is constant along an entire length of the lumen in the direction of the longitudinal axis.

4. The connector of claim 1, wherein the first diameter is different than the second diameter.

5. The connector of claim 1, wherein the connector body and the luer body are integrally formed with one another.

6. The connector of claim 1, wherein each of the plurality of ribs extends perpendicular to the longitudinal axis, and wherein each of the plurality of ribs forms a ring extending around the longitudinal axis.

7. The connector of claim 1, wherein the connector provides a shear rate of less than 50 s-1 for the fluid flowing therein for a flow rate between 300 mL/min and 5000 mL/min.

8. The connector of claim 1, wherein the connector is a single inlet, single outlet connector such that no more than two flexible tubing segments may couple to the connector.

9. An assembly comprising:

a connector comprising a connector body having a first end defining a first opening and a second end defining a second opening disposed opposite one another along a linear longitudinal axis of the connector body, the connector body defining:

a first bore extending from the first end toward the second end, the first bore having a circular cross-sectional shape and a first diameter;

a second bore extending from the second end toward the first end, the second bore having a circular cross-sectional shape and a second diameter;

a lumen extending from the first bore to the second bore, the lumen having a circular cross-sectional shape and a third diameter that is less than each of the first diameter and the second diameter, wherein the first bore, the second bore, and the lumen are coaxial with the linear longitudinal axis; and a luer body configured for removably coupling with a mating luer adapter, wherein the luer body is coupled to the connector body and extends perpendicular to the longitudinal axis, the luer body defining a second lumen in fluid communication with the lumen of the connector body, wherein the connector body has a hexagonal cross-sectional shape defined by one or more external surfaces, the connector body further comprising a plurality of ribs each extending outwardly from the one or more external surfaces;

a first flexible tubing segment comprising a first end portion received within the first opening of the first bore, the first flexible tubing segment having a first outer diameter and a first inner diameter, the first inner diameter being equal to a diameter of the lumen adjacent the first bore; and a second flexible tubing segment comprising a second end portion received within the second opening of the second bore, the second flexible tubing segment having a second outer diameter and a second inner diameter, the second inner diameter being equal to a diameter of the lumen adjacent the second bore, wherein a smooth flow path from the first flexible tubing segment, through the lumen, and to the second flexible tubing segment is formed, the flow path minimizing zones of stagnation, recirculation, and low shear rate of a fluid flowing therein.

10. The assembly of claim 9, wherein the connector provides a shear rate of less than 50 s-1 for the fluid flowing therein for a flow rate between 300 mL/min and 5000 mL/min.

11. The assembly of claim 9, wherein the connector is a single inlet, single outlet connector such that no more than two flexible tubing segments may couple to the connector.

12. The assembly of claim 9, wherein each of the plurality of ribs forms a ring extending around the longitudinal axis.

13. A connector for connecting flexible tubing segments, the connector comprising:

a connector body having a first end defining a first opening and a second end defining a second opening disposed opposite one another along a linear longitudinal axis of the connector body, the connector body defining:

a first bore extending from the first end toward the second end and configured for receiving an end portion of a first flexible tubing segment therein, the first bore having a circular cross-sectional shape and a first diameter;

a second bore extending from the second end toward the first end and configured for receiving an end portion of a second flexible tubing segment therein, the second bore having a circular cross-sectional shape and a second diameter; and a lumen extending from the first bore to the second bore, the lumen having a circular cross-sectional shape and a third diameter that is less than each of the first diameter and the second diameter, wherein the first bore, the second bore, and the lumen are coaxial with the linear longitudinal axis, wherein the lumen varies in diameter symmetrically about the longitudinal axis along at least a portion of a length of the lumen in the direction of the longitudinal axis, wherein the connector is a single inlet, single outlet connector having no more than two openings such that no more than two flexible tubing segments may couple to the connector, and wherein the connector body is sized such that when the first flexible tubing segment is inserted into the first bore via the first opening and the second flexible tubing segment is inserted into the second bore via the second opening, a smooth flow path from the first flexible tubing segment, through the lumen, and to the second flexible tubing segment is formed, the flow path minimizing zones of stagnation, recirculation, and low shear rate of a fluid flowing therein, wherein the connector body has a hexagonal cross-sectional shape defined by one or more external surfaces, the connector body further comprising a plurality of ribs each extending outwardly from the one or more external surfaces, and wherein each of the plurality of ribs forms a ring extending around the longitudinal axis.

14. The connector of claim 13, wherein the lumen comprises:

a first portion extending from the first bore and having a constant diameter; and a second portion extending from the first portion to the second bore and having a varying diameter in the direction of the longitudinal axis.

15. The connector of claim 14, wherein the diameter of the second portion varies in a linear manner in the direction of the longitudinal axis.

16. The connector of claim 14, wherein the diameter of the second portion varies in a non-linear manner in the direction of the longitudinal axis.

17. The connector of claim 13, wherein the lumen varies in diameter along an entire length of the lumen in the direction of the longitudinal axis.

18. The connector of claim 13, wherein the first diameter is different than the second diameter.

* * * * *